(12) United States Patent
Galli

(10) Patent No.: US 6,689,341 B2
(45) Date of Patent: *Feb. 10, 2004

(54) DESENSITIZING DENTAL COMPOSITION

(75) Inventor: Giovanna Galli, Florence (IT)

(73) Assignee: Italmed S.n.c. di Galli G. e Pacini G., Florence (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/623,578

(22) PCT Filed: May 20, 1998

(86) PCT No.: PCT/EP98/02963

§ 371 (c)(1), (2), (4) Date: Sep. 6, 2000

(87) PCT Pub. No.: WO99/44570

PCT Pub. Date: Sep. 10, 1999

(65) Prior Publication Data

US 2003/0194381 A1 Oct. 16, 2003

(30) Foreign Application Priority Data

Mar. 6, 1998 (IT) ............................... FI98A0051

(51) Int. Cl.$^7$ ............................ A61K 7/16; A61K 6/00; A61K 6/02
(52) U.S. Cl. ..................... 424/49; 424/57; 433/215; 433/216; 433/228.1; 106/35
(58) Field of Search .................. 424/49–58; 106/35; 433/215, 216, 228.1

(56) References Cited

U.S. PATENT DOCUMENTS

| | | | | |
|---|---|---|---|---|
| 5,234,971 A | * | 8/1993 | Imai et al. ................ | 424/51 |
| 5,522,726 A | * | 6/1996 | Hodosh ................... | 433/215 |
| 5,534,244 A | * | 7/1996 | Tung ...................... | 424/57 |
| 5,603,922 A | * | 2/1997 | Winston et al. ........... | 424/57 |
| 5,874,066 A | * | 2/1999 | Hack, I et al. ............ | 424/49 |
| 5,879,663 A | * | 3/1999 | Nakabayashi et al. ...... | 424/57 |
| 5,906,809 A | * | 5/1999 | Hack, II et al. ........... | 424/49 |

* cited by examiner

Primary Examiner—Shep K. Rose
(74) Attorney, Agent, or Firm—Simpson & Simpson, PLL

(57) ABSTRACT

A dental composition for the treatment of dentinal hypersensitivity and in particular for the desensitization of exposed dentin, the desensitizing treatment of deep cavities, the desensitizing treatment when replacing dental layers, the stumps desensitizing treatment before placing dental prosthesis. The composition can be used as a solution or as a gel. In the first case two distinct liquid solutions for use successively on the exposed dentin are provided for. In the second case two distinct gel compounds spread successively on the exposed dentin are provided for. The first solution or the first gel compound comprises preferably three soluble potassium salts, whereas the second solution or the second gel compound comprises a calcium salt and a soluble strontium salt. In a preferred composition two solutions are provided for of which the first has solutes comprising potassium phosphate, potassium carbonate and potassium fluoride, and the second solution has solutes comprising calcium chloride and strontium chloride. For the gel composition, which may be used as toothpaste, two distinct gel compounds are provided, the first having solutes comprising potassium phosphate, potassium carbonate and potassium fluoride and the second gel compound having solutes comprising calcium chloride and strontium chloride.

10 Claims, No Drawings

DESENSITIZING DENTAL COMPOSITION

FIELD OF THE INVENTION

The present invention generally relates to a compound for dentistry and, more precisely, it relates to a dental composition for the treatment of dentinal hypersensitivity.

In particular, the composition is suitable for the desensitization of the exposed dentin, such as, in particular, for
- the desensitizing treatment of deep cavities,
- the desensitizing treatment when replacing dental layers,
- the stumps desensitizing treatment before placing dental prosthesis.

The composition can be used as a solution or as a gel.

DESCRIPTION OF THE PRIOR ART

Dentinal hypersensitivity is a problem often met by dentists in their patients and is often intensified when eating hot or cold food, sweet or acidulous food, as well as when brushing teeth.

Normal dentin is covered by enamel (crown dentin) or by cement (radicular dentin) and is not permeable.

In teeth sensitive zones enamel is found often eroded or worn away and dentin exposed. In other cases, gingival recession uncovers the most sensitive portions of the teeth, i.e. the junction enamel-cement.

The absence of cover exposes the dentinal tubules. In addition, pulp is rich of nerves many of which are centrifugally directed towards dentin. Dentin is crossed radially by dentinal tubules which contain dentinal fluid. Through the tubules a nervous stimulus reaches sensorial areas of the dental pulp.

A first known way to reduce dentinal sensitivity is to close the orifices of dentinal tubules. To this extent, natural substances are known able to reduce sensitivity by closing the tubules, such as tartar, collagen or mineral salts precipitated in saliva.

Chemical compounds, like solutions, gel compounds to or pastes, as well as physical treatments are also known capable of mechanically obliterating the orifices of the dentinal tubules. Compounds of the s kind are known in GS2239601 and in WO 92/04006.

Other compounds or treatments or this kind are:
- potassium and iron oxalate, which react with ionised calcium present in the saliva and form calcium oxalate which Precipitates and obliterates the dentinal tubules orifices;
- silver nitrate which acts through the precipitation of silver compounds;
- tin fluoride, which acts through the precipitation of tin compounds;
- strontium salts;
- insoluble salts such as calcium phosphate, hydroxyapatite, colloidal silica etc. which directly obliterate the tubular orifices;
- glass-ionomeric cement;
- some types of resins.

Other compounds, known for example in U.S. Pat. No. 5,603,922 or in WO-A-97/06774, provide a composition useful to remineralize lesions in dental enamel. Hypersensitivity is counteracted as a secondary effect, owing to the obliteration of dentin due to remineralization.

In any case the obliteration of the dentinal tubules by means of soluble or insoluble salts used up to now, even if they are simple to use, is not enough effective and last only a short time.

Compounds are known, moreover, such as potassium chloride or nitrate or oxalate capable of reducing the dentinal sensitivity through a depolarising effect of the nervous fibres, without obliterating the dentinal tubules. Therefore, desensitization treatments are known using said compounds, capable of stopping the pulpal nervous activity by varying the dentinal tubules nervous fibres excitability. However, also in this case, the effect duration is short.

New techniques, not yet used in clinical practice, use glass-ionomeric cement or photo-induced resins. Desensitization is improved, but they are not easy to use and are good for deep erosions only.

Moreover, treatments are known using either laser or ultrasounds scalers, which cause the formation of smear layers and tubules obliteration. These treatments give results, such as effectiveness and duration, similar to the topical treatment with the above described soluble or insoluble salts, but they require expensive apparatus.

SUMMARY OF THE INVENTION

It is an object of the present invention to provide a dental composition for dentinal desensitization which has good mechanical obliteration properties of the dentinal tubules in addition to depolarising properties of the nervous dentinal fibres, arid is capable of obtaining good effectiveness and long duration, as well as of being easy to use.

According to a first aspect of the invention, this object is reached by the composition whose characteristic is to comprise at least two solutions to be used successively on the exposed dentin.

A second aspect of the invention provides at least two distinct gel compounds to be used successively on the exposed dentin.

The characteristics of said solutions and said gel compounds is to comprise a first and a second solution or a first and a second gel, suitable for being mixed topically, wherein:

- in the first solution a first solute consisting in potassium phosphate and at least a second solute selected among potassium carbonate, potassium fluoride, potassium oxalate, are present, and
- in the second solution a first solute selected among a calcium salt and at least a second solute selected among a strontium salt, a silver salt, a barium salt, a zinc salt are present,
- whereby a crystal complex is formed comprising
  - a plurality of insoluble salts having obliterating properties on the dentinal tubules obtained by double exchange reaction of the first and second solute of the first and second solution,
  - a soluble potassium salt having depolarising effect on dentin.

The preferred general weight ratio for the firs solution is the following:

| | |
|---|---|
| potassium phosphate | 0,5–20% |
| potassium carbonate | 0,5–10% |
| potassium fluoride | 0,1–5% |
| sodium methylparaben | 0,1% |
| deionized water | 64,9–98,8% |

The preferred general weight ratio for the second solution is the following:

| | |
|---|---|
| calcium chloride | 0,5–20% |
| strontium chloride | 0,5–11% |
| benzoate sodium | 0,2% |
| deionized water | 68,8–98,8% |

The preferred general weight ratio for the first gel compound is the following:

| | |
|---|---|
| potassium phosphate | 0,5–10% |
| potassium carbonate | 0,5–5% |
| potassium fluoride | 0,1–0,5% |
| sorbitol | 30–45% |
| colloidal silica | 15–30% |
| glycerol | 5–10% |
| carboxy methyl hydroxy ethyl cellulose | 0,5–1,5% |
| lauryl sulphate sodium | 1.–1,5% |
| benzoate sodium | 0,3–0,8% |
| saccharinated sodium | 0,3–0,5% |
| mint fragrance | q.s. |
| colour CI 42051, CI 19140 | q.s. |
| purified water | q.s. 100 ml |

The preferred general weight ratio for the second gel compound is the following:

| | |
|---|---|
| strontium chloride | 0,5–10% |
| calcium chloride | 0,5–10% |
| sorbitol | 30–45% |
| colloidal silica | 15–30% |
| glycerol | 5–10% |
| carboxy methyl hydroxy ethyl cellulose | 0,5–1,5% |
| lauryl sulphate sodium | 1–1,5% |
| benzoate sodium | 0,3–0,8% |
| saccharinated sodium | 0,3–0,5% |
| mint fragrance | q.s. |
| colour CI 16255, CI 47005 | q.s. |
| purified water | q.s. 100 ml |

The combined use of the two preferred solutions or of the two preferred gel compounds successively has the result, after an immediate double exchange reaction, of six insoluble salts:

calcium phosphate, calcium carbonate, calcium fluoride, strontium phosphate, strontium carbonate, strontium fluoride, and a soluble salt, i.e. potassium chloride.

According to a sudden reaction a "crystal complex" is formed by said six insoluble salts which surprisingly have shown desensitizing properties in the short term (15 minutes) and in the long term (6–12 months).

The formation of the potassium chloride helps to increase the desensitization properties adding a nervous depolarising effect. In fact, potassium chloride is obtained after a double exchange reaction and is present in solution inside the dentinal tubule when the "crystal complex" is formed which obliterates the tubules orifices. In this way a higher amount of potassium is present for a longer time with respect to the depolarising compounds according to the prior art, which do not obliterate the dentinal tubules, thus allowing the dentinal fluid (whose flow is always centrifugal) and then also the potassium ions to come out the dentinal tubules.

The use of an induced crystallisation for obliterating the dentinal tubules with the formation of a "crystal complex" along with the formation (always inside the tubules) of a compound with depolarising properties of the nervous fibres, is new in the dental field, and is used with excellent results according to the present invention.

If the composition according to the invention is prepared with potassium phosphate, potassium carbonate and potassium fluoride (for the first solution) in amounts higher than 20, 10 and 5% respectively for the first solution and with calcium chloride and strontium chloride in amounts higher than 20 and 11% respectively for the second solution, a desensitizing is obtained having the same good properties as above described, but less convenient to use. In fact, at the moment of the union of the two solutions, when the formation of the six insoluble salts occurs, an opalescent gel compound would result, less handy and less spreadable on the surface to cure.

It is also advisable that the two solutions are spread with different brushes so that the two solutions or gels are not in contact before they reach the patient's mouth.

Similarly, the composition with potassium phosphate, potassium carbonate and potassium fluoride in amounts higher than 10, 5 and 0.5% for the first gel compound and with calcium chloride and strontium chloride in amounts higher than 10% for both the salts of the second gel compound, a desensitizing composition is obtained which can be used having the same properties as above described, but less suitable for a toothpaste because its organoleptic aspect would be less acceptable.

The composition according to the present invention, will be made clearer with the not limitative following examples.

EXAMPLE 1.1

A composition for desensitizing exposed dentin which uses two solutions to be spread successively comprises potassium phosphate, potassium carbonate and potassium fluoride for the first solution and calcium chloride and strontium chloride for the second solution, with the following weight ratio:

| | |
|---|---|
| Solution n° 1 | |
| potassium phosphate | 16% |
| potassium carbonate | 5% |
| potassium fluoride | 3% |
| sodium methylparaben | 0.1% |
| deionized water | 75,9% |
| Solution n° 2 | |
| calcium chloride | 16% |
| strontium chloride | 10,6% |
| benzoate sodium | 0.2% |
| deionized water | 73,2% |

The preferred spreading method is the following for the desensitizing treatment: after having isolated the surgical area with cotton elements or the like and after having ablated the dental plaque by means of low speed electric brushing, the surface to be treated is cleaned by cotton pellets wet by a disinfectant liquid (such as sodium hypochlorite 5% solution). Then the surface is dried with air jet for about 15 seconds. The drying action must substantially dehydrate the external layer of the exposed dentin . Then, by means of a brush or cotton pellets or spongy elements gently rubbed, the first solution is spread for about 20 seconds. Immediately after the second solution is spread onto the same dental surface and in the same way.

When hypersensitivity is high, the same treatment can be repeated.

The action of such a composition, which reacts forming a crystal complex which deeply obliterates the dentinal tubules orifices is double. In fact, the first solution spread on the dehydrated dentin causes, for capillarity, the filling of the dentinal tubules. To this the nervous depolarisation is added of the potassium chloride which always forms inside the tubules through a double exchange reaction.

Alternatively to the composition of the above example 1, in the same way the following exemplifying compositions can be used. In these compositions only two potassium salts are present in the first solution and the crystal complex will be formed by 4 insoluble salts only. Soluble potassium salts are still present.

EXAMPLE 1.2

| Solution n° 1 | |
| --- | --- |
| potassium phosphate | 16% |
| potassium oxalate | 6% |
| sodium methylparaben | 0.1% |
| deionized water | q.s. 100 ml |
| Solution n° 2 | |
| calcium chloride | 16% |
| strontium chloride | 10% |
| benzoate sodium | 0.2% |
| deionized water | 73,8% |

EXAMPLE 1.3

| Solution n° 1 | |
| --- | --- |
| potassium phosphate | 16% |
| potassium carbonate | 5% |
| sodium methylparaben | 0.1% |
| deionized water | q.s. 100 ml |
| Solution n° 2 | |
| calcium chloride | 16% |
| barium chloride | 10% |
| benzoate sodium | 0.2% |
| deionized water | 73,8% |

EXAMPLE 1.4

| Solution n° 1 | |
| --- | --- |
| potassium phosphate | 16% |
| potassium carbonate | 5% |
| sodium methylparaben | 0.1% |
| deionized water | q.s. 100 ml |
| Solution n° 2 | |
| calcium chloride | 16% |
| silver chloride | 10% |
| benzoate sodium | 0.2% |
| deionized water | 73,8% |

EXAMPLE 1.5

| Solution n° 1 | |
| --- | --- |
| potassium phosphate | 16% |
| potassium carbonate | 5% |
| sodium methylparaben | 0.1% |
| deionized water | q.s. 100 ml |
| Solution n° 2 | |
| calcium chloride | 16% |
| zinc chloride | 10% |
| benzoate sodium | 0.2% |
| deionized water | 73,8% |

EXAMPLE 1.6

| Solution n° 1 | |
| --- | --- |
| potassium phosphate | 16% |
| potassium carbonate | 5% |
| sodium methylparaben | 0.1% |
| deionized water | 78,9% |
| Solution n° 2 | |
| calcium chloride | 16% |
| strontium chloride | 10,6% |
| benzoate sodium | 0.2% |
| deionized water | 73,2% |

EXAMPLE 2

A desensitizing composition to be used as a toothpaste which uses sequentially two gel compounds comprising potassium phosphate, potassium carbonate and potassium fluoride for the first gel compound and calcium chloride and strontium chloride for the second gel compound, with the following weight ratio:

| Gel compound n° 1 | |
| --- | --- |
| potassium phosphate | 8% |
| potassium carbonate | 3,5% |
| potassium fluoride | 0,4% |
| sorbitol | 30% |
| colloidal silica | 15% |
| glycerol | 5% |
| lauryl sulphate sodium | 1,5% |
| carboxy methyl hydroxy ethyl cellulose | 1% |
| benzoate sodium | 0,5% |
| saccharinated sodium | 0,4% |
| mint fragrance | q.s. |
| colour CI 42051, CI 19140 | q.s. |
| purified water | q.s. 100 ml |
| Gel compound n° 2 | |
| calcium chloride | 7% |
| strontium chloride | 6% |
| sorbitol | 30% |
| colloidal silica | 15% |
| glycerol | 5% |
| lauryl sulphate sodium | 1,5% |
| carboxy methyl hydroxy ethyl cellulose | 1% |
| benzoate sodium | 0,5% |
| saccharinated sodium | 0,4% |
| mint fragrance | q.s. |
| colour CI 16255, CI 47005 | q.s. |
| purified water | q.s. 100 ml |

This composition is used in the following way for the desensitizing treatment:

on the toothbrush an amount of gel compound n°1 substantially equal to the volume of two peas is poured;

both dental arches are spread with gel compound n°1 by brushing from the above to the bottom for about two minutes;

the friction is prolonged on the areas which are sensitive to hot or cold food, to acidulous or sweet substances;

without rinsing, after having spread on the toothbrush the same amount of gel compound n°2, the same dental surface is brushed again as above described for the first gel compound;

after the two gel compounds have mixed on the dental surface an instant double exchange reaction occurs with the formation of the "crystal complex", comprising the six insoluble salts and potassium chloride;

then the mouth is rinsed with water.

The foregoing description of specific embodiments will so fully reveal the invention according to the conceptual point of view, so that others, by applying current knowledge, will be able to modify and/or adapt for various applications such embodiments without further research and without departing from the invention, and it is therefore to be understood that such adaptations and modifications will have to be considered as equivalent to the specific embodiments. The means and the materials to realise the different functions described herein could have a different nature without, for this reason, departing from the field of the invention. It is to be understood that the phraseology or terminology employed herein is for the purpose of description and not of limitation.

What is claimed is:

1. A method for depolarizing dentin and obliterating dentinal tubule orifices of a subject with hypersensitive dentin, which comprises the steps of:

providing a first liquid solution or gel comprising potassium phosphate as a first solute and at least a second solute comprising one other potassium salt selected from the group consisting of potassium carbonate, potassium fluoride and potassium oxalate;

providing a second liquid solution or gel comprising a calcium salt as a first solute and at least a second solute selected from the group consisting of a salt of strontium, silver, barium and zinc;

topically applying said first and second liquid solutions or gels to the dentinal tubule orifices in the dentin of a subject with hypersensitive dentin in need of dentinal depolarization and obliteration of dental tubules, and mixing topically on said dentinal tubule orifices on said hypersensitive dentin to form a dental desensitizing composition comprising the first and second solutions or gels to generate a crystal complex inside the dental tubules comprising a plurality of insoluble salts obtained by double exchange reaction of said salts, and further soluble potassium salt, wherein said insoluble salts have an obliterating effect on the dentinal tubules, said soluble potassium salt having a depolarizing effect on said dentin.

2. The method according to claim 1, wherein the first solute in said second liquid solution is a member selected from the group consisting of calcium chloride and calcium acetate, and the second solute is a member selected from the group consisting of strontium chloride, strontium acetate, silver chloride, barium chloride and zinc chloride.

3. The method o according to claim 1, wherein said first solute in said second gel is calcium chloride and the second solute is strontium chloride.

4. The method according to claim 1, wherein said first and second liquid solutions or gels comprise a solvent and a bacteriostatic preservative.

5. The method according to claim 4 wherein the solutes of the first solution are potassium phosphate, potassium carbonate and potassium fluoride; and the solutes for the second solution are calcium chloride and strontium chloride, and are present in the following general weight ratio:

| Solution no. 1 | |
|---|---|
| potassium phosphate | 0,5–20% |
| potassium carbonate | 0,5–10% |
| potassium fluoride | 0.5–5% |
| Preservative | 0.1% |
| Solvent | 64.9–98.4% |
| Solution no. 2 | |
| calcium chloride | 0.5–20% |
| strontium chloride | 0.5–10% |
| Preservative | '0.2% |
| Solvent | 69.8–98.8% |

6. The method according to claim 5 wherein said solvent is deionized water and said preservative is sodium methylparaben for said solution no. 1 and benzoate sodium for said solution no. 2.

7. The method according to claim 6 wherein said solutes, solvent, and preservative are present in the following weight ratio:

| Solution no. 1 | |
|---|---|
| potassium phosphate | 16% |
| potassium carbonate | 5% |
| potassium fluoride | 3% |
| sodium methylparaben | 0.1% |
| deionized water | 75.9% |
| Solution no. 2 | |
| calcium chloride | 15% |
| strontium chloride | 10.6% |
| benzoate sodium | 0.2% |
| deionized water | 74,2% |
| Preservative | 0.2% |
| Solvent | 69.8–98.8% |

8. The method according to claim 4, wherein in said first liquid solution, said at least second solute is potassium oxalate; and in said second liquid solution the first solute is a member selected from the group consisting of calcium chloride and acetate and the second solute is selected from the group consisting of strontium chloride, strontium acetate, silver chloride, barium chloride and zinc chloride, and said solvent is deionized water and said preservative is sodium methylparaben for the first solution and benzoate sodium for the second solution.

9. The method according to claim 3 for use as gel toothpaste suitable for desensitizing exposed dentin, wherein the solutes for the first gel are potassium phosphate, potassium carbonate and potassium fluoride and the solutes for the second gel are calcium chloride and strontium chloride and the other compounds are present according to the following general weight ratio:

| Gel compound no. 1 | |
|---|---|
| potassium phosphate | 0.5–10% |
| potassium carbonate | 0.5–5% |
| potassium fluoride | 0.1–0.5% |
| sorbitol | 30–45% |
| colloidal silica | 15–30% |
| glycerol | 5–10% |
| carboxy methyl hydroxy ethyl cellulose | 0.5–1.5% |
| lauryl sulphate sodium | 1–1.5% |
| benzoate sodium | 0.3–0.8% |
| saccharinated sodium | 0.3–0.5% |
| mint fraqrance | qs. |
| colour CI 42051, CI 19140 | qs. |
| purified water | qs. 100 ml |
| Gel compound no. 2 | |
| strontium chloride | 0.5–10% |
| calcium chloride | 0.5–10% |
| sorbitol | 30–45% |
| colloidal silica | 15–30% |
| glycerol | 5–10% |
| carboxy methyl hydroxy ethyl cellulose | 0.5–1.5% |
| lauryl sulphate sodium | 1–1.5% |
| benzoate sodium | 0.3–0.8% |
| saccharinated sodium | 0.3–0.5% |
| mint fragrance | qs. |
| colour CI 16255, CI 47005 | qs. |
| purified water | qs. 100 ml |

10. The method according to claim 8 wherein said solutes and the other compounds are present in the following weight ratio:

| Gel compound no. 1 | |
|---|---|
| potassium phosphate | 8% |
| potassium carbonate | 3.5% |
| potassium fluoride | 0.4% |
| sorbitol | 30% |
| colloidal silica | 15% |
| qlycerol | 5% |
| lauryl sulphate sodium | 1.5% |
| carboxy methyl hydroxy ethyl cellulose | 1% |
| benzoate sodium | 0.5% |
| saccharinated sodium | 0.4% |
| mint fragrance | qs. |
| colour CI 42051, CI 19140 | qs. |
| purified water | qs. 100 ml |
| Gel compound no.2 | |
| calcium chloride | 7% |
| strontium chloride | 6% |
| sorbitol | 30% |
| colloidal silica | 15% |
| glycerol | 5% |
| lauryl sulphate sodium | 1.5% |
| carboxy methyl hydroxy ethyl cellulose | 1% |
| benzoate sodium | 0.5% |
| saccharinated sodium | 0.4% |
| mint fragrance | qs. |
| colour CI 16255, CI 47005 | qs. |
| purified water | qs. 100 ml |

* * * * *

UNITED STATES PATENT AND TRADEMARK OFFICE
CERTIFICATE OF CORRECTION

PATENT NO.    : 6,689,341 B2
DATED         : February 10, 2004
INVENTOR(S)   : Giovanna Galli It is certified that error appears in the above-identified patent and that said Letters Patent is hereby corrected as shown below:

Column 8,
Lines 45-46, delete "Preservative    0.2%" and "Solvent  69.8-98.8%"

Signed and Sealed this

Twenty-ninth Day of June, 2004

JON W. DUDAS
*Acting Director of the United States Patent and Trademark Office*